US009335244B2

(12) United States Patent
Han

(10) Patent No.: US 9,335,244 B2
(45) Date of Patent: May 10, 2016

(54) SYSTEM AND METHOD FOR CONVERTING OPTICAL DIAMETERS OF AEROSOL PARTICLES TO MOBILITY AND AERODYNAMIC DIAMETERS

(75) Inventor: Hee-Siew Han, Maple Grove, MN (US)

(73) Assignee: TSI INCORPORATED, Shoreview, MN (US)

( * ) Notice: Subject to any disclaimer, the term of this patent is extended or adjusted under 35 U.S.C. 154(b) by 0 days.

(21) Appl. No.: 14/236,372

(22) PCT Filed: Aug. 8, 2012

(86) PCT No.: PCT/US2012/049994
§ 371 (c)(1),
(2), (4) Date: Mar. 31, 2014

(87) PCT Pub. No.: WO2013/022971
PCT Pub. Date: Feb. 14, 2013

(65) Prior Publication Data
US 2014/0247450 A1    Sep. 4, 2014

Related U.S. Application Data

(60) Provisional application No. 61/521,614, filed on Aug. 9, 2011.

(51) Int. Cl.
G01N 21/00    (2006.01)
G01N 15/02    (2006.01)
G01N 15/00    (2006.01)
G01N 15/14    (2006.01)
G01N 15/10    (2006.01)

(52) U.S. Cl.
CPC ........ *G01N 15/0211* (2013.01); *G01N 15/1459* (2013.01); *G01N 2015/0003* (2013.01); *G01N 2015/0046* (2013.01); *G01N 2015/1075* (2013.01); *G01N 2015/1497* (2013.01)

(58) Field of Classification Search
USPC .......... 356/335–343; 250/574, 287, 299, 282; 73/28.05, 28.01, 865.5, 863.22, 61.72, 73/335.01; 324/71.4
See application file for complete search history.

(56) References Cited

U.S. PATENT DOCUMENTS

| 4,473,296 A | 9/1984 | Shofner et al. |
| 7,932,490 B2 | 4/2011 | Wang et al. |
| 8,047,055 B2 | 11/2011 | Wang et al. |

(Continued)

OTHER PUBLICATIONS

Hudson et al., "A Newly Designed and Constructed Instrument for Coupled Infrared Extinction and Size Distribution Measurements of Aerosols." Aerosol Science and Technology, 41:701-710, 2007, entire document especially p. 703, col. 2-704, col. 1.

(Continued)

*Primary Examiner* — Tri T Ton
(74) *Attorney, Agent, or Firm* — Kagan Binder, PLLC

(57) ABSTRACT

A system and a method of measuring a particle's size in a select aerosol using the optical diameter of the particle to perform a mobility and/or aerodynamic diameter conversion without any knowledge about the particle's shape and its optical properties in the aerosol being characterized. In one example embodiment of the invention, the method includes generating a set of calibration data and finding the optimal refractive index and shape that best fits the calibration data. In addition, the method includes creating a new calibration curve that provides a mobility-equivalent or aerodynamic-equivalent diameter.

8 Claims, 12 Drawing Sheets

(56) References Cited

U.S. PATENT DOCUMENTS

| | | | |
|---|---|---|---|
| 2004/0025567 A1 | 2/2004 | Marjamaki et al. | |
| 2007/0180936 A1* | 8/2007 | Zeng | 73/865.5 |
| 2009/0039249 A1 | 2/2009 | Wang et al. | |
| 2010/0288921 A1 | 11/2010 | Wang et al. | |
| 2012/0012744 A1 | 1/2012 | Wang et al. | |

OTHER PUBLICATIONS

Khlystov et al., "An Algorithm for Combining Electrical Mobility and Aerodynamic Size Distributions Data when Measuring Ambient Aerosol." Aerosol Science and Technology, 38(S1):229-238, (2004), entire document.

DeCarlo et al., "Particle Morphology and Density Characterization by Combined Mobility and Aerodynamic Diameter Measurements. Part 1: Theory." Aerosol Science and Technology, 38:1185-1205, 2004, entire document.

Jennifer L. Hand et al., A New Method for Retrieving Particle Refractive Index and Effective Density from Aerosol Size Distribution Data, Aerosol Science and Technology, 36:10, 1012-1026, DOI: 10.1080/02786820290092276, Nov. 30, 2010.

Jennifer L. Hand, Dissertation: A New Technique for Obtaining Aerosol Size Distributions with Applications to Estimates Size of Aerosol Properties, Department of Atmospheric Science, Colorado State University, Summer 2001.

Extended European Search Report, EP Patent Application No. 12822091.0-1553/2741843, Mar. 2, 2015.

* cited by examiner

SYSTEM AND METHOD FOR CONVERTING OPTICAL DIAMETERS OF AEROSOL PARTICLES TO MOBILITY AND AERODYNAMIC DIAMETERS

CLAIM OF PRIORITY AND CROSS REFERENCE TO RELATED APPLICATION

The present application claims priority to International Application No. PCT/US2012/049994, filed on Aug. 8, 2012, which in turn claims the benefit of U.S. Provisional Application No. 61/521,614, filed Aug. 9, 2011, and is related to U.S. Pat. No. 7,932,490 issued on Apr. 26, 2011, the disclosures of which are hereby incorporated by reference in their entireties.

BACKGROUND OF THE INVENTION

Aerosols commonly found in the environment are generated both by nature and human activity. They influence human lives in many ways. Aerosols in the atmosphere can absorb and/or scatter light and change visibility as well as the earth energy balance. Atmospheric aerosols also serve as condensation sites for cloud formation, thus playing an important role in the climate. When inhaled, aerosol particles can deposit on the respiratory track and cause adverse health effects.

Industry and government have recognized the importance of measuring and monitoring aerosol concentrations in the environment or workplace so that proper measure can be taken to reduce potential health risks. Pertinent monitoring applications include but are not limited to industrial/occupational hygiene surveys, outdoor ambient/site perimeter monitoring for dust control operations, and engine emission studies. Some industrial processes require knowledge of the particulates in the environment, including environments having a sparse population of particles (e.g., semiconductor manufacturing) as well as environments having an extensive presence of particle populations (e.g., dry powder manufacturing processes).

In 1987, the United States Environmental Protection Agency (EPA) revised the National Ambient Air Quality Standards (NAAQS) and started to use mass of particles with aerodynamic diameters less than approximately 10 .μm (hereinafter "the PM10") as the particulate matter (PM) pollution index. The PM10 is an index of the PM that can enter the thorax and cause or exacerbate lower respiratory tract diseases, such as chronic bronchitis, asthma, pneumonia, lung cancer, and emphysema. It was later determined that PM concentrations in the air, as indexed by the mass of particles with aerodynamic diameters less than approximately 2.5 .μm ("PM2.5") was more closely associated with the annual mortality rates than with the coarser PM10. In 1997, in its next revision of the NAAQS, the EPA promulgated regulations on PM2.5. Recently, there has been extensive discussion on the health effects of particles smaller than 1 μm (i.e. "PM1").

The American Conference of Governmental Industrial Hygienists (ACGIH) has also established sampling conventions of respirable, thoracic and inhalable aerosols, defined as particles having aerodynamic diameters of less than 4 μm, 10 μm, and 100 μm respectively. Inhalable particles are those capable of entering through the human nose and/or mouth during breathing. Thoracic particles are the inhaled particles that may penetrate to the lung below the larynx. Respirable particles are the inhaled particles that may penetrate to the alveolar region of the lung. A discussion of the various sampling conventions are found at National Primary and Secondary Ambient Air Quality Standards, 40 Code of US Federal Regulation, Chapter 1, Part 50 (1997) and Vincent, J. H., Particle Size-Selective Sampling for Particulate Air Contaminants Cincinnati, ACGIH (1999), both of which are hereby incorporated by reference except for explicit definitions contained therein.

While the aforementioned standards and conventions are based on the aerodynamic diameters of particles, it is understood that size segregated mass concentration groupings (e.g., PM1, PM2.5, PM10, respirable, thoracic and inhalable) may be based on the optical particle diameters instead of the aerodynamic diameters for purposes of the instant application. That is, PM2.5 (for example) may approximate particles having an aerodynamic diameter of less than approximately 2.5 μm or particles having an optical diameter of less than approximately 2.5-μm.

One instrument that measures particle size dependent number concentrations in real time is the optical particle counter (OPC). In an OPC, particles pass through an interrogation volume that is illuminated by a light beam. The light scattered by each particle is collected on to a detector to generate an electrical pulse. From the pulse height (i.e. the intensity of the scattered radiation) one can infer the particle size based on prior calibration. Because the size inferred from the OPC depends on the particle optical properties, the inferred parameter is often referred to as the "optical equivalent particle size." By assuming aerosol properties such as density, shape and refractive index, the size distribution can be converted to mass distribution, such as described by Binnig, J., J. Meyer, et al. "*Calibration of an optical particle counter to provide PM2.5 mass for well-defined particle materials*," Journal of Aerosol Science 38(3): 325-332 (2007), which is hereby incorporated by reference herein other than express definitions of terms specifically defined therein. Some advantages of the OPC are: (1) particles may be counted with high accuracy for low particle concentrations; (2) favorable signal to noise ratios for particle sizes greater than 1 μm; and (3) low cost. However, the inferred particle optical size may not be the same as the actual or geometric particle size because the determination depends on the particle shape and refractive index assumptions.

Another instrument that measures particle size distribution in real time is an Aerodynamic Particle Sizer (APS), such as described in U.S. Pat. No. 5,561,515 to Hairston et al., assigned to the assignee of the instant application, the disclosure of which is hereby incorporated by reference herein other than express definitions of terms specifically defined therein. When particles of different sizes are accelerated through an accelerating nozzle, larger particles may tend to be accelerated to a lesser extent through the interrogation volume(s) than smaller particle because the larger particles may possess a greater inertia to overcome. The APS exploits this principle by accelerating particles through a nozzle to obtain size dependent particle velocities, which are typically measured by measuring the time-of-flight of the particles through the sensing zone. Unlike the OPC measurement, the APS measurement is independent of the particle refractive index. Also, while converting the particle size distribution to mass distribution, the APS is less sensitive to the particle density parameter than the OPC measurement. Good agreement between the mass concentrations calculated from APS spectra and from direct mass measurements has been demonstrated in the size range of 0.5- to 10-μm. See Sioutas, C. (1999). "Evaluation of the Measurement Performance of the Scanning Mobility Particle Sizer and Aerodynamic Particle Sizer." Aerosol Science and Technology 30(1): 84-92.

A shortcoming of the APS is that only particle populations of relatively low concentration (e.g., on the order of 1000- particle/cm$^3$ and lower) can be measured due to coincidence error. For example, the TSI Model 3321 APS accurately measures aerodynamic particle size distributions in the 0.5- to 20-µm range, (with 5% coincidence error) up to approximately 1000-particles/cm$^3$. The APS resolution decreases with the particle size. Also, all commercially available instruments are relatively expensive.

The TSI Model 3321 APS utilizes the aerodynamic particle diameters of the detected particles to calculate the mass concentration of the aerosol. Effectively, the mass of each detected particle is calculated assuming the particle to be spherical and of known density. Calibration factors may also be applied to account for correct the nonspherical shape and differing density of the particles. Inherent limitations to this approach are that the mass calculation is not based on detection of the smaller diameter particles (less than approximately 0.3-µm optical or aerodynamic diameter) that go undetected by the APS or OPC detector. Also, this approach is limited to low concentration applications.

In spite of several shortcomings, there are numerous arguments in favor of using optical particle counters (OPCs) to measure particle size distribution and to perform mass concentration measurement. To make the OPCs more robust and address some of the shortcomings, there is a need to develop a method or measurement system to convert optical diameters to measures of diameter related to aerosol particle physical behavior, such as electrical mobility (or simply mobility) and/or aerodynamic diameters. This conversion is advantageous because mobility diameters are more commonly used for submicron particles (particles with sizes smaller than 1 µm), while aerodynamic diameters are commonly used in areas such as aerobiology, heath effect studies, mass measurement, etc. This conversion can be done if the optical properties of the aerosols of interest are known, and the particles in aerosols are spherical. However, most of the aerosols of interest have particles of irregular shape and their optical properties are usually unknown as well, so the conversion cannot be easily made.

SUMMARY OF THE INVENTION

The optical particle counter (OPC) is one of the most widely used aerosol instruments because of its low cost and ability to rapidly provide particle size distributions in real time. OPCs measure the size and number concentration of aerosol particles by means of light scattering by single particles. As each particle passes through a focused light beam, it scatters a pulse of light to a photodetector, which is then converted to an electric signal. The focused light beam could come from a white light or laser source. The electric signal is usually an electronic pulse. This pulse is analyzed and the pulse height or area is then correlated to particle size and the count is distributed to the proper size channel, where the total counts in each size range are accumulated. In addition to the particle size, the amount of light scattered by the particle also depends on the particle properties, namely refractive index and shape.

Particle diameters measured by OPCs are usually referred to as optical diameters. Since almost all commercially available OPCs are factory-calibrated with polystyrene latex (PSL) particles, sometimes the diameters are also referred to as PSL-equivalent diameters. Nevertheless, in most of the applications, optical diameters or PSL-equivalent diameters usually are not very useful, and they need to be converted to measures of diameter related to their physical behavior, such as electrical mobility (or simply mobility) and/or aerodynamic diameters. This conversion is necessary because mobility diameter is more commonly used for particles smaller than 1 µm, while aerodynamic diameters are more commonly used in areas such as aerobiology, health effect studies, environmental monitoring, etc. The conversion can be done if aerosol particles are spherical in shape and their refractive indices are known since the light scattering and extinction by a spherical particle can be described and modeled by the Mie scattering theory. Unfortunately, except for certain laboratory generated aerosol particles, aerosols of interest are usually irregular in shape and/or their refractive indices are unknown.

Size distributions of airborne particles often span a wide size range from a few nanometers to several micrometers, which typically exceeds the measurement size range of any single instrument. Therefore, researchers often combined data from multiple instruments. One such combination is that of electrical mobility-based instrument such as the scanning mobility particle sizer (SMPS) and light scattering-based instrument such as the optical particle counter (OPC). The SMPS is regarded as the gold standard for submicron aerosol size distribution measurement. Depending on the configuration, it can cover the size range from 2.5 nm to 1 µm. The OPC is one of the most widely used instruments for coarse particles especially in areas such as filter testing, indoor air quality, cleanroom monitoring, etc. Typical OPC size range is 0.3 to 10 µm.

The SMPS and OPC have different measurement principles. The SMPS classifies particles according to their electrical mobilities, and for spherical particles, the electrical mobility sizes are same as the geometric sizes. The OPC, on the other hand, measures sizes according to the amount of light scattered by the particles. The light scattering phenomenon can be described by the Mie scattering theory. The sizes measured by the OPC are typically referred to as optical diameters. Because of the different measurement principles, in order to combine SMPS and OPC distributions into a single size spectrum, particle shape factors and refractive indices are needed. Unfortunately, except for some laboratory generated aerosols, shape factors and refractive indices of aerosols of interest are typically unknown. In this study we attempted to fit the optical particle size distributions to the SMPS distributions for aerosols with known and unknown refractive indices. For aerosols with known refractive indices, the optical size distributions were adjusted with Mie scattering calculation. If refractive indices were unknown, an additional calibration step was performed. Several laboratory generated aerosols with known refractive indices were used to evaluate the method. The method was then further evaluated with various ambient aerosols with unknown refractive indices.

The various embodiments of the inventive concept disclosed herein disclose a system and a method that can measure a particle's size in a select aerosol using the optical diameter of the particle to perform a mobility and/or aerodynamic diameter conversion without any knowledge about the particle's shape in the aerosol being characterized and its optical properties. In one example embodiment of the invention, the method includes generating a set of calibration data and finding the optimal refractive index and shape that best fits the calibration data. In addition, the method includes creating a new calibration curve that provides a mobility-equivalent or aerodynamic-equivalent diameter.

DETAILED DESCRIPTION OF THE INVENTION

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 1:
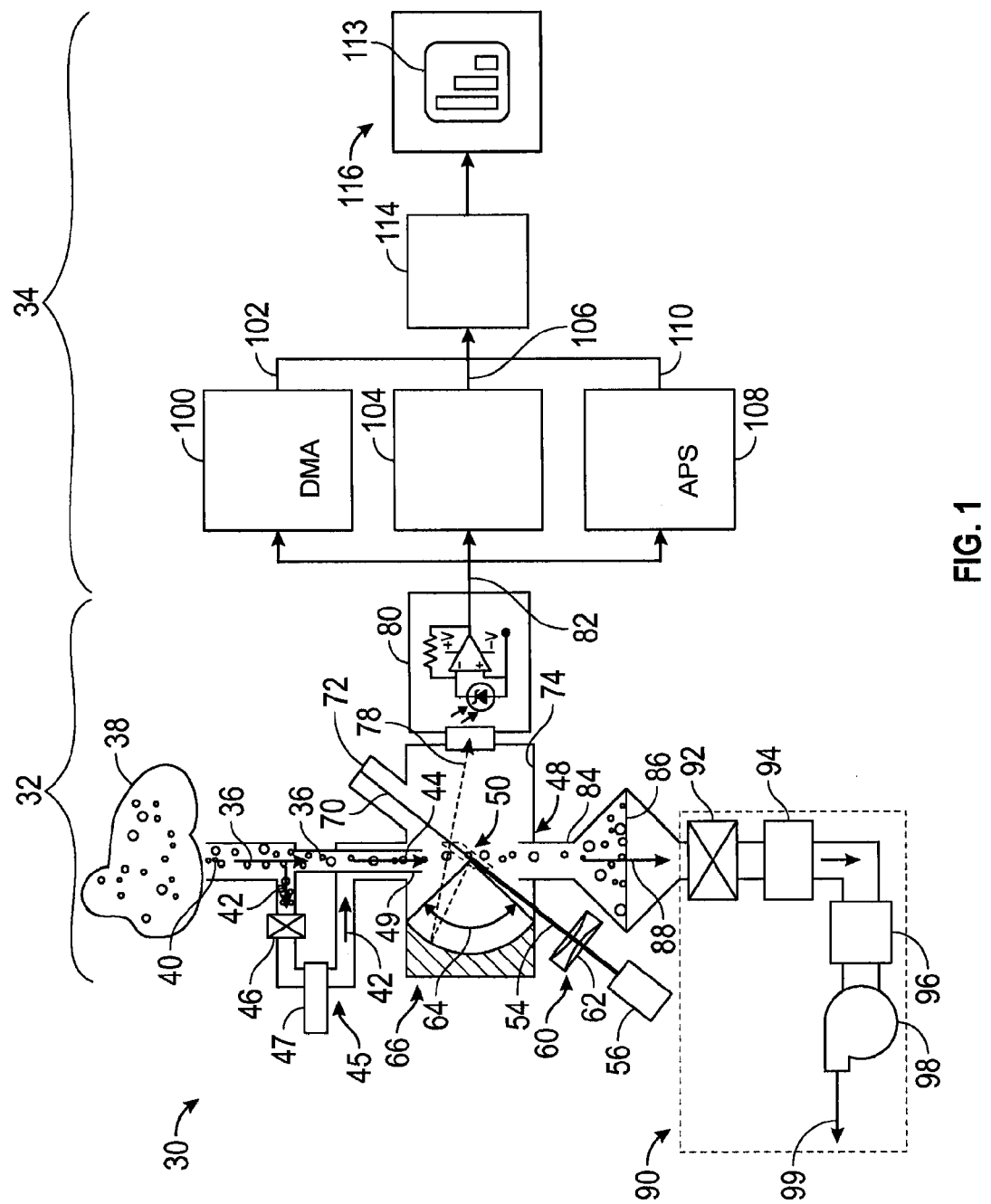
FIG. 1 is a schematic diagram depicting a particle size measurement system in an embodiment of the invention.

Referring to FIG. 1, a particle size measurement system 30 comprising an aerosol measurement section 32 and a calibration and processing section (CAPS) 34 is schematically depicted in an embodiment of the invention. An incoming flow stream 36 may be drawn from an aerosol cloud 38 through an inlet 40 of the aerosol measurement section 32. The incoming flow stream 36 may be split into a sheath flow stream 42 and an aerosol flow stream 44 having particles that are targeted for measurement. The sheath flow stream 42 may be diverted to a sheath flow conditioning loop 45 that may include a filtration device 46 and a flow measuring device 47. The aerosol flow stream 44 may be passed through an inlet nozzle 49 to an optics chamber 48 that includes a viewing or interrogation volume 50. The interrogation volume 50 may be defined by the intersection of a light beam 54 and the aerosol flow stream 44. The light beam 54 may be sourced from an electromagnetic radiation source 56 such as a diode laser, a LED or a lamp (broadband or line emitting). In a related embodiment (discussed later herein; see FIG. 8), the sheath flow comes from air that is exhausted from blower 98 which is then filtered and re-routed to loop 45 to act as sheath flow 42 before reaching nozzle 49.

In this example embodiment, particle size measurement system 30 includes beam shaping optics 60 that may include a lens 62 such as a cylindrical lens. The shaping optics 60 may additionally or alternatively comprise reflective components such as mirrors, or fiber optic components (not depicted). A portion of the light scattered from particles over a solid angle 64 may be subtended by a light collection system or radiation collector 66 (e.g., a spherical mirror, aspheric condenser lenses, or other electromagnetic radiation collection devices available to the artisan) within the optics chamber 48. An unscattered portion 70 of the light beam 54 may be captured by a light trap 72. Inner surfaces 74 of the optics chamber 48 may be coated with a black or high absorptivity coating such as an anodized coating. Collected light 78 gathered by the radiation collector 66 may be transferred to a detector 80 such as a photodiode or a photomultiplier tube. The detector 80 may produce an electrical signal 82 proportional to the convolution of the incident electromagnetic radiation and the spectral sensitivity of the detector 80.

In some embodiments, the aerosol flow stream 44 exits the optics chamber 48 through an outlet nozzle 84 and may be passed through a gravimetric filter 86, thereby producing a pre-filtered aerosol flow stream 88. The aerosol flow streams 44 may be drawn through the optics chamber 48 by a pumping system 90 that includes a protection filter 92, a flowmeter 94, a flow pulsation damping chamber 96 and a pump or blower 98 that is ducted to an exhaust 99. Numerous kinds of pumps or blowers may be utilized, including but not limited to a diaphragm pump, a rotary vane pump, a piston pump, a roots pump, a linear pump or a regenerative blower.

In one embodiment, the CAPS 34 may condition the electrical signal 82 to define three different signal circuits: a dynamic mobility diameter signal circuit 100 for generating mobility diameter data/outputs 102 associated with the particles of the collected light 78 gathered by the radiation collector 66 and incident on the detector 80; a pulse height conditioner circuit 104 for detecting scattered light originating from individual particles as they pass through the interrogation volume 50 and generating pulse height outputs 106 in accordance therewith; and an aerodynamic diameter signal circuit 108 generating aerodynamic diameter data/outputs 110 that provide (direct or indirect) measurement of the size of the particles being measured as they pass through the interrogation volume 50. The outputs 102, 106 and 110 may be routed to a digital processor module 114 for calibration and subsequent conversion into a particle size distribution 113. The result can be output to a device 116, such as a display, a storage device, analog output or a computer.

Functionally, beam shaping optics 60 may be utilized to configure the shape of the light beam 54 and interrogation volume 50 to possess certain characteristics, such as overall width and height, as well as intensity profile. The light trap 72 mitigates or prevents biasing of the electrical signal 82 that may be caused by the unscattered portion 70 of the light beam 54 gathered by the radiation collector 66 after multiple scattering within the optics chamber 48. When utilized, the high absorptivity coating on the inner surfaces 74 of the optics chamber 48 may further reduce the propagation of stray light. In operation, mobility diameter circuit 100 provides data akin to that produced by a differential mobility analyzer device while pulse height output 106 and aerodynamic diameter data/output 110 are akin to the outputs of OPC and APS devices, respectively.

Particles can be collected on the gravimetric filter 86 and can be weighed to measure mass directly. This direct mass measurement can be used to create the calibration relationship between the electrical signal 82 and the mass of the collected particles (see discussion attendant FIG. 9 of U.S. Pat. No. 7,932,490 and the Binnig 2007 paper referenced herein). Particles on the gravimetric filter 86 can also be analyzed to study their chemical compositions. The protection filter 92 may remove particles remaining in the air stream 88 upstream of the flowmeter 94 and pump or blower 98 for protection against particle contamination, especially in configurations where there is no gravimetric filter in place. The pump or blower 98 may be used to drive the flow through the whole system. The flow pulsation damping chamber 96 is an optional device that may reduce the pulsation of flow in the system.

The filtration device 46 of the sheath flow conditioning loop 45 removes particulate matters from the sheath flow stream 42 to provide a substantially clean flow of gas that shrouds or sheaths the aerosol flow 44. The cleansed sheath flow 42 helps contain particulates within the core of the aerosol flow 44 as it passes through the optics chamber 48, thereby mitigating against particulate contamination of the optics chamber 48 and appurtenances therein. The flow measuring device 47, when utilized, can provide an indication of the flow rate of the sheath flow stream 42 which can be subtracted from the total flow rate of the incoming flow stream 36 provided by the flowmeter 94 to determine the flow rate of the aerosol flow stream 44.

The optical particle counter (OPC) is one of the most widely used aerosol instruments because of its low cost and ability to rapidly provide particle size distributions in real time. OPCs measure the size and number concentration of aerosol particles by means of light scattering by single particles. In addition to the particle size, the amount of light scattered by the particle also depends on the particle properties, namely refractive index and shape.

Particle diameters measured by OPCs are usually referred to as optical diameters or PSL-equivalent diameters. Nevertheless, in most of the applications, optical diameters usually are not very useful, and they need to be converted to measures of diameter related to their physical behavior, such as electrical mobility and/or aerodynamic diameters. This conversion is necessary because mobility diameter is more commonly used for particles smaller than 1 μm, while aerodynamic diameters are more commonly used in areas such as aerobiology, health effect studies, environmental monitoring, etc. The conversion can be done if aerosol particles are spherical in shape and their refractive indices are known since the light scattering and extinction by a spherical particle can be described and modeled by the Mie scattering theory. Unfortunately, except for certain laboratory generated aerosol particles, aerosols of interest are usually irregular in shape and/or their refractive indices are unknown. The following description provides more detail on the overall measurement system and on the operation of CAPS module 34 which eventually helps to generate more accurate and robust particle size measurement data by using calibration data generated along with Mie scattering modeling.

Figure 1A:
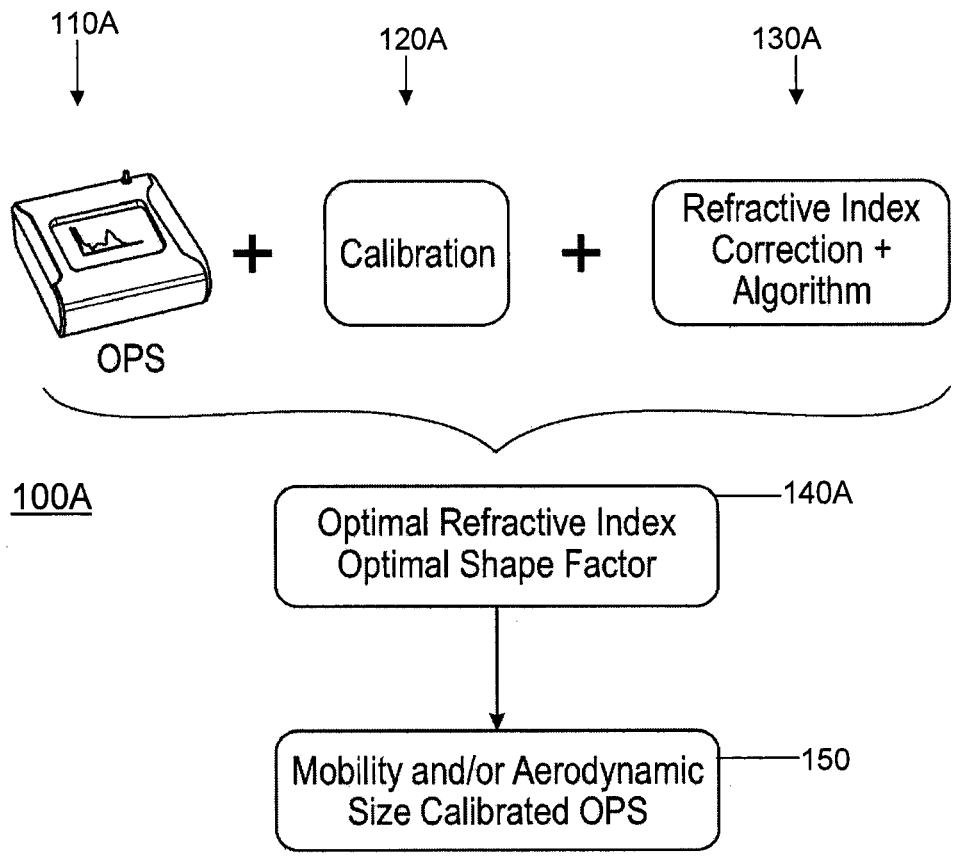
FIG. 1A is a depiction of the system and method for converting optical diameters into mobility and/or aerodynamic diameters.

Referring now to FIG. 1A, in one example embodiment of a measurement system 100A for particles in an aerosol to be measured with an optical particle sizer (OPS) 110A, which uses therein an OPC, that is operatively coupled to a calibration system 120A and a refractive index and a shape factor system 130A. Together, OPS 110A, calibration system 120A and system 130A optimize the refractive index and the shape factor in 140A thereby generating mobility and/or aerodynamic size calibrated OPS 150A. In general, the method of the present invention consists of three main steps: (1) generating a set of calibration data; (2) finding the optimal refractive index and shape that best fits the calibration data; and (3) creating new calibration curves that provide mobility-equivalent or aerodynamic-equivalent diameters. In this figure, the OPS is represented by a TSI 3330 Optical Particle Sizer (which includes an OPC).

Figure 2:
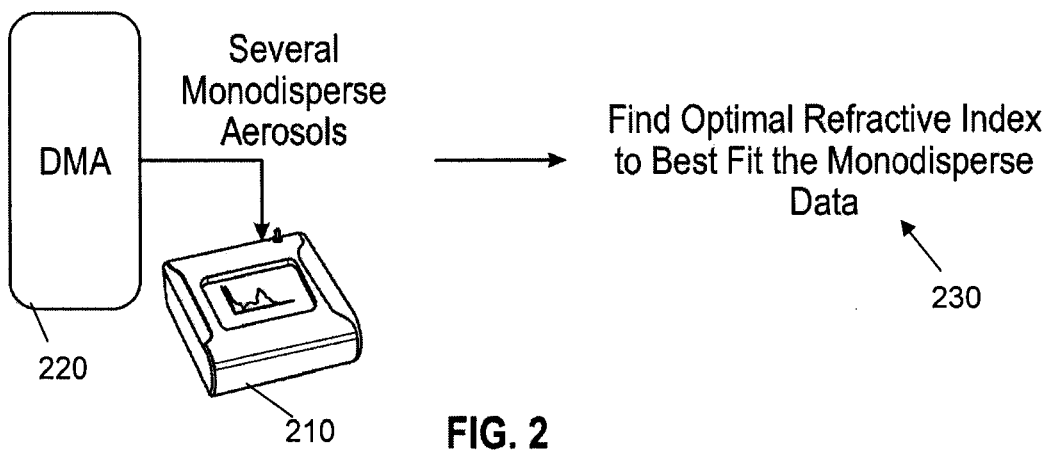
FIG. 2 depicts the calibration procedure for converting optical diameters to mobility diameters.
Figure 3:
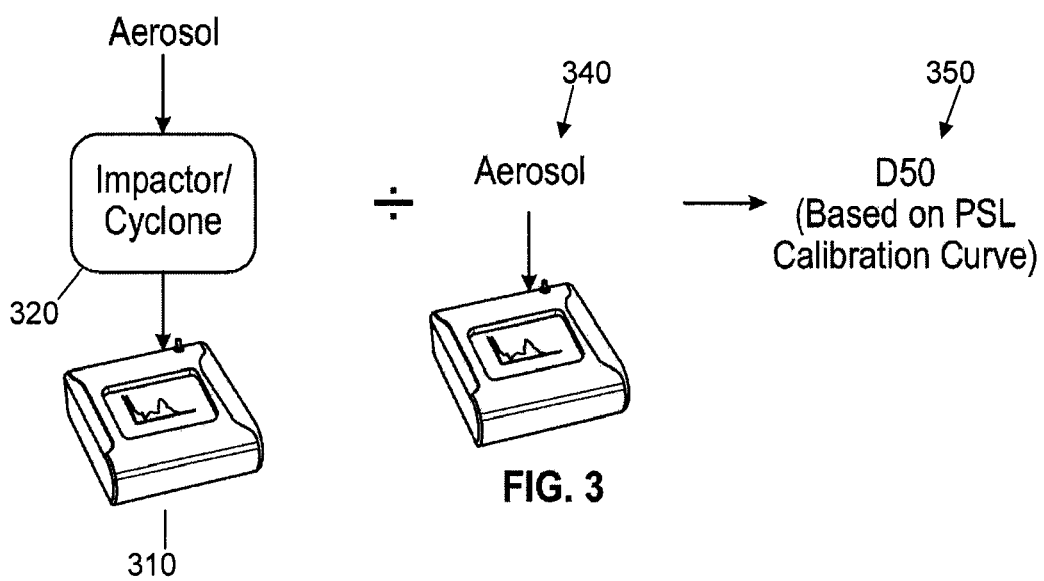
FIG. 3 depicts the calibration procedure for converting optical diameters to aerodynamic diameters.
Figure 4:
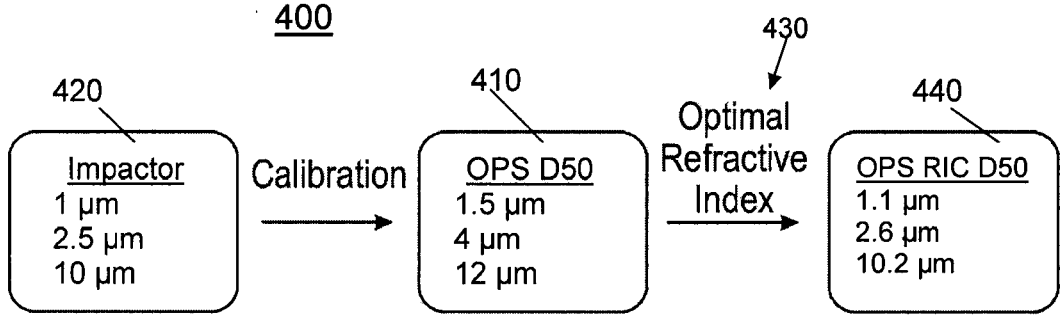
FIG. 4 depicts an example flow of a conversion from optical diameter to aerodynamic diameter.

Referring now to FIGS. 2-4, the calibration steps for mobility and aerodynamic diameters are different as will be discussed herein. For generating calibration data for the mobility diameter application, a calibration system 200 uses an OPC 210 and a differential mobility analyzer (DMA) 220 and involves generating several differential mobility analyzer classified monodisperse aerosols and subsequently measuring them with the OPC. Next, system 200 optimizes the refractive index to best fit the monodisperse data at step 230.

Referring now to FIG. 3, in generating calibration data for an aerodynamic diameter application (which can include a number of different ways to generate aerodynamic data depending on the set up and components used), for the sake of simplicity, we focus on system 300 and on data generated with impactors or cyclones 320. The size distribution of the particles in the aerosol of interest is measured by an OPC 310 with and without the impactor or a cyclone. At step 340, a cut point of impactor or cyclone 320 is then determined by taking the ratio of the two OPC distributions generated on the previous step. Since the OPC response is based on a factor-calibrated PSL curve (350), the cut point measured by the OPC is not expected to be the same as the impactor/cyclone cut point which is defined using the aerodynamic diameter. By using several different cut point impactors or cyclones, a set of calibration data can be obtained. Once the calibration data is determined, a Mie scattering (modeling) calculation is then performed to find the refractive index that best fits the calibration data. In a related embodiment, a shape factor is also included in the calculation to improve the accuracy. In this example embodiment, the refractive index and shape factor that provide the best fit to the calibration data are referred to as optimal refractive index and optimal shape factor. A new mobility-equivalent or aerodynamic-equivalent calibration curve is then created using this optimal refractive index and shape factor.

Referring now to FIG. 4, in this example embodiment OPS 410 of system 400 is calibrated with impactors 420 with cut points 1, 2.5 and 10 μm using the calibration steps described in FIG. 3. Since the OPS measures optical or PSL-equivalent diameters, the cut points measured are different from the impactor cut points which are based on aerodynamic diameters. In this example embodiment, OPS 410 responses for impactors 420 are 1.5, 4 and 12 μm. A Mie scattering calculation program 430 is then used to find the optimal refractive index and shape factor so that cut points measured with the OPS are as close as possible to the known impactor cut points of 1, 2.5 and 10 μm. As shown in FIG. 4, OPS 410 measured cut points after refractive index and shape factor correction (RIC) are found to be 1.1, 2.6, and 10.2 μm at step 440. Ideally, we would like these values exactly the same as the impactor cut points 1, 2.5 and 10 μm. In practice, however, accuracy is limited by instrument resolution, the number of calibration point as well as particle properties. Once the optimal refractive index and shape factor are determined, a new calibration curve is generated and the OPS can now be used to measure aerodynamic diameter equivalent diameter for this aerosol.

Figure 5:
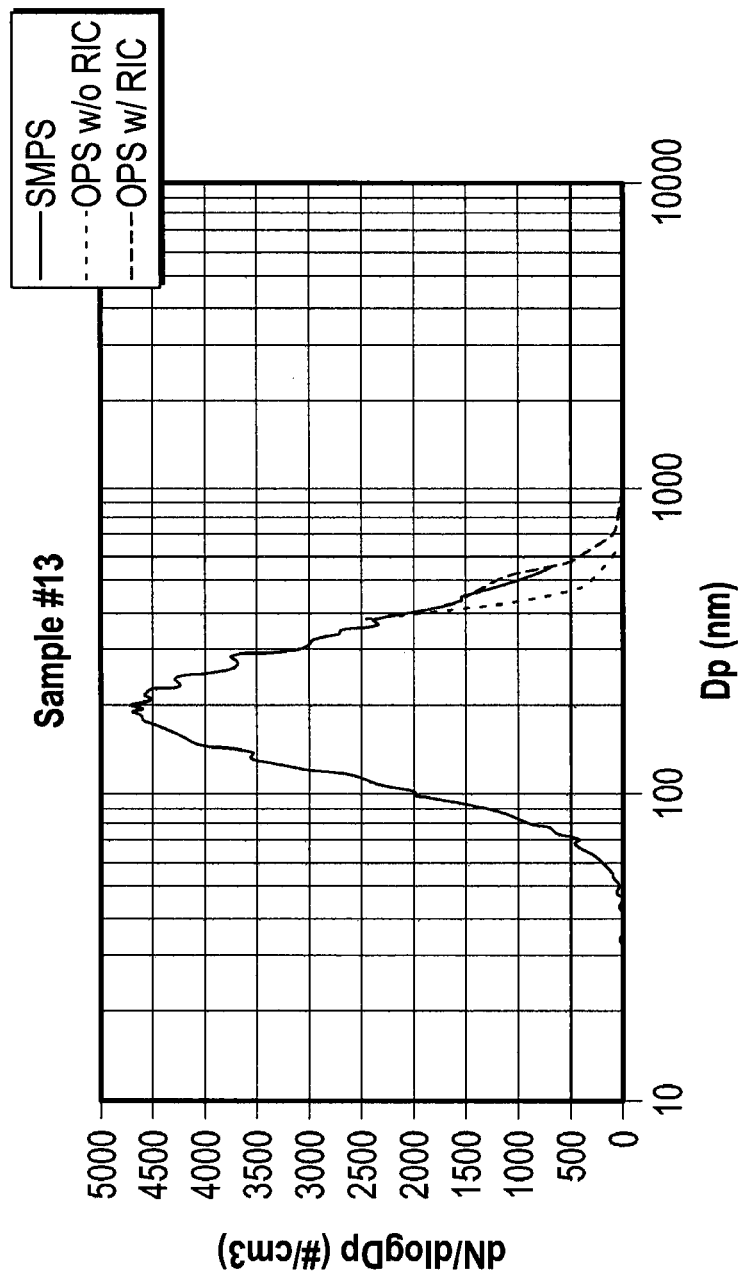
FIG. 5 depicts particle distributions measured with an optical sizer and a mobility diameter sizer.
Figure 6:
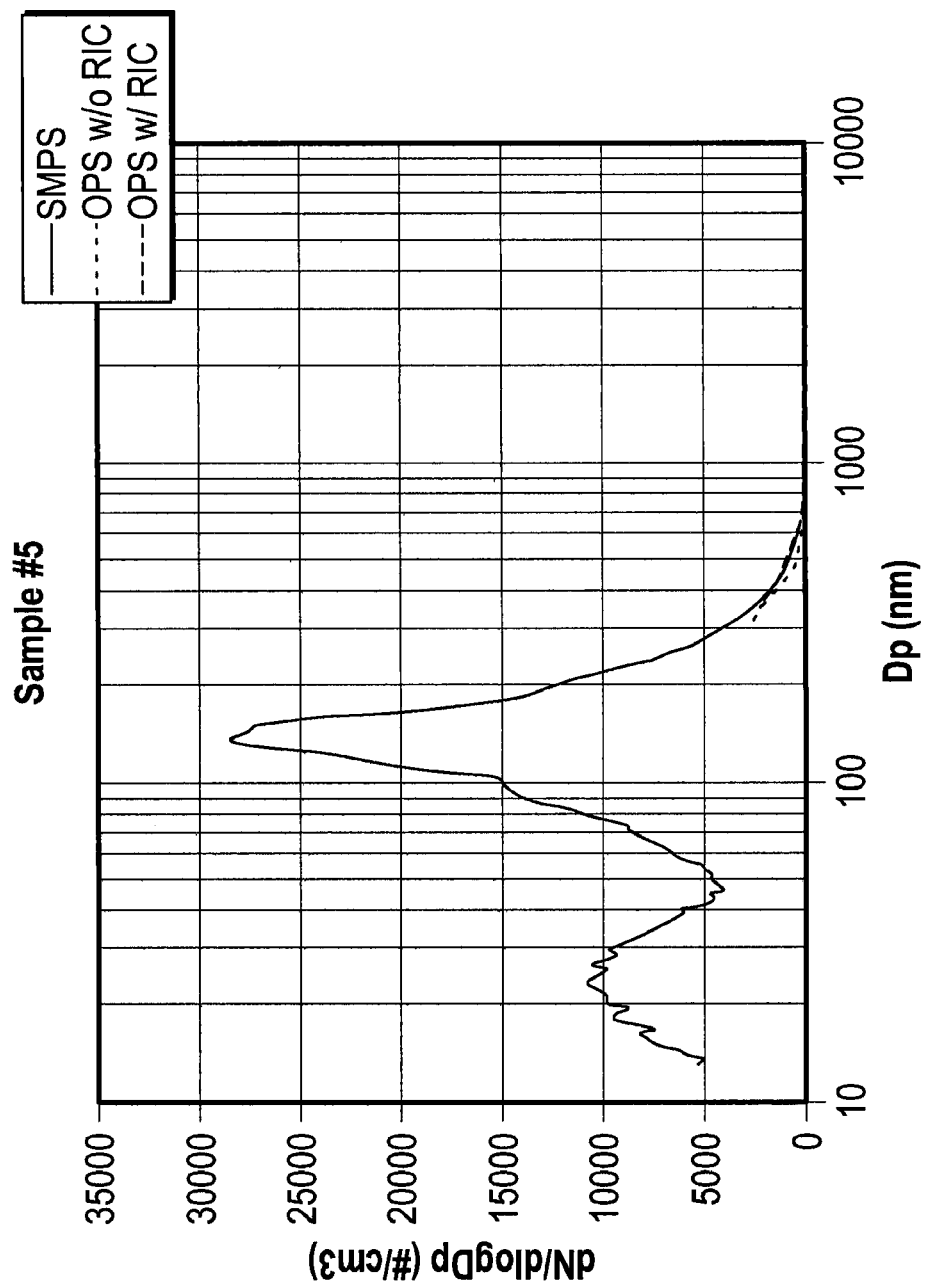
FIG. 6 depicts particle size distribution measured at a physical facility.
Figure 8:
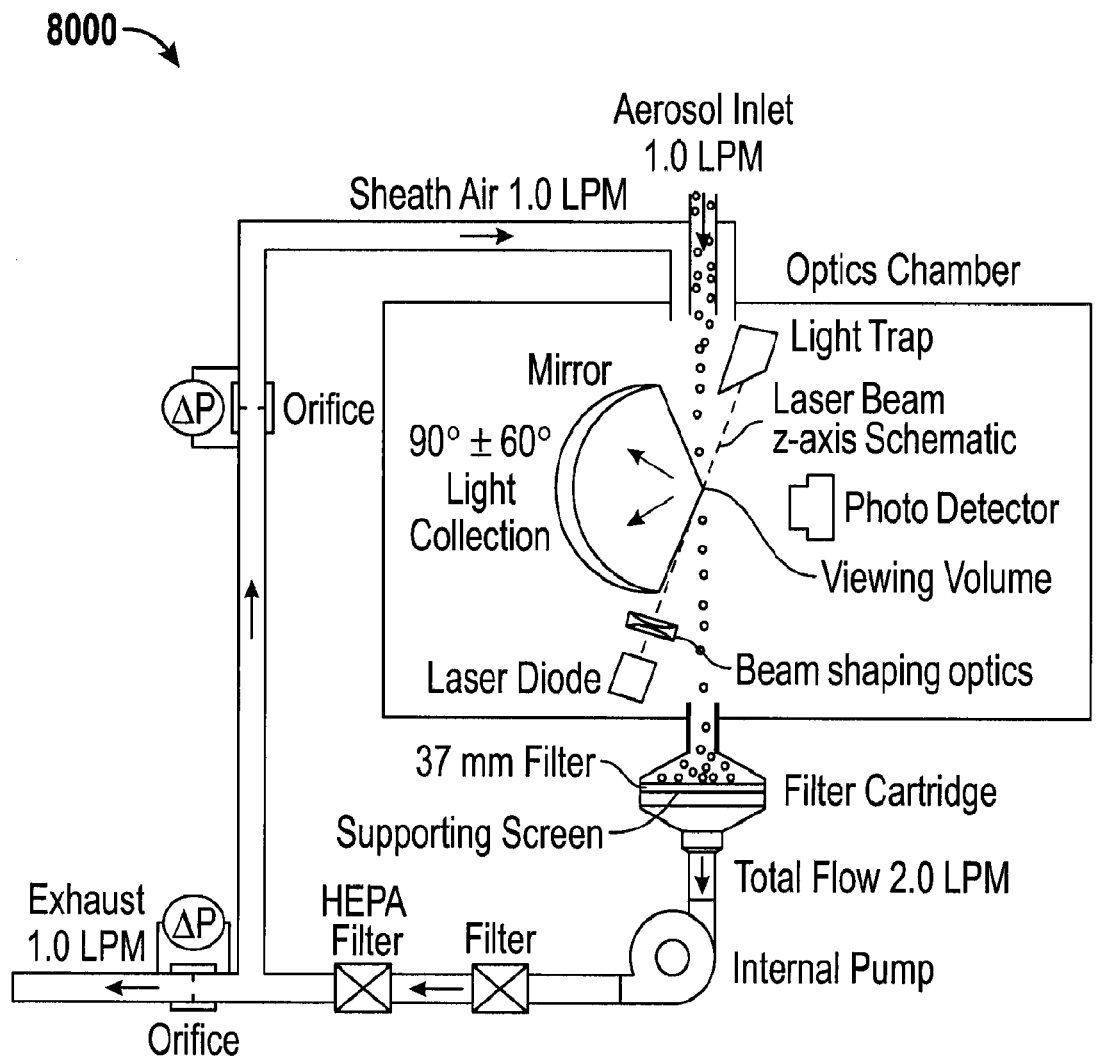
FIG. 8 depicts a measurement system using a SMPS and OPS to measure particle size over a wide range.

One application of a mobility-diameter-calibrated OPC of system 200 is that it can be combined with a Scanning Mobility Particle Sizer (SMPS) for wide range particle size distribution measurement (see FIG. 8). Since the typical SMPS size range is from a few nanometers (nm) to about 500 nm, and an OPC size range is from 300 nm to 10 μm, combining these two instruments would allow size distribution measurement from a few nanometers to about 10 μm. FIG. 5 shows an example of particle size distributions (Sample #13) measured with an SMPS and OPS. It is clear that the OPS distribution after the RIC merges better than the one without the RIC to generate a more accurate and consistent curve of measurement of the wide particle size range. FIG. 6 shows particle size distributions measured in a designated smoking area (Sample #5), with a second peak (around 150 nm) shown in the figure to be particles generated from cigarettes.

Figure 7A:
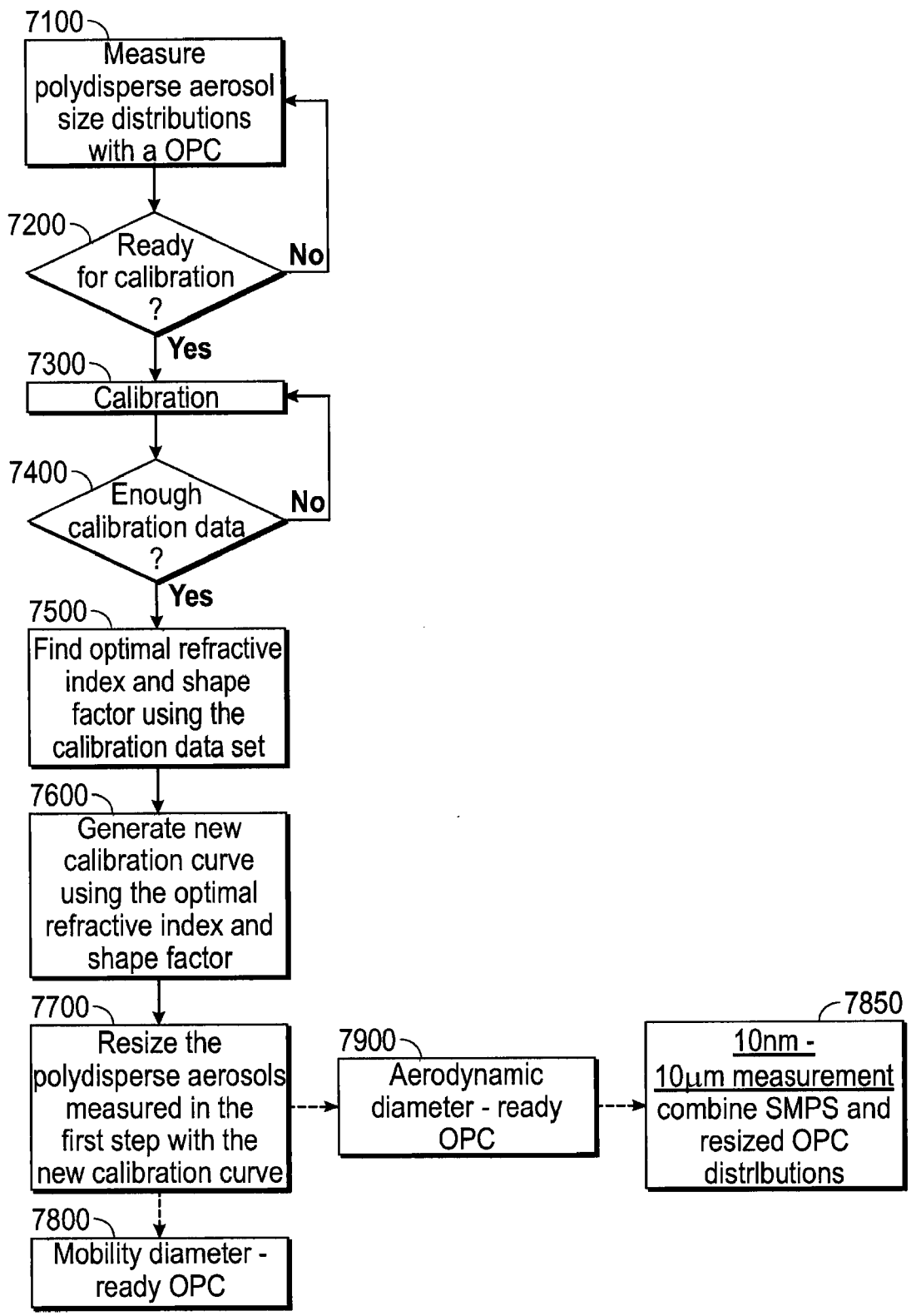
FIGS. 7A-7F are various flowcharts that illustrate various components of the calibration process and the optical to mobility/aerodynamic diameter conversion method.

Referring now to FIGS. 7A-7F, there are illustrated various flowcharts that describe various components of the calibration process and the optical to mobility/aerodynamic diameter conversion method. In particular, FIG. 7A is the top level flowchart showing the steps to modifying an optical particle sizer and/or an optical detector to arrive at a mobility diameter-ready OPC device 7800 or an aerodynamic diameter-ready OPC device 7900. In this example embodiment, the device 7800 will be used as described in box 7850 to measure particles from about 10 nanometers (nm) to about 10 micrometers (μm), which is to combine an SMPS and resized OPC distributions.

Referring more specifically to FIG. 7A, a method of recalibrating an OPC includes the step 7100 of measuring polydisperse aerosol size distributions with an OPC, after which the system requests at step 7200 if the OPC is ready for calibration. If the OPC is not ready, the user determines how often to do the calibration depending, among other factors, if there are, for instance, rapidly changing aerosols (which may require more calibrations). If the OPC is ready for calibration, then proceed to a calibration procedure 7300, which can be the calibration procedure 7300A (FIG. 7B) for mobility-diameter ready OPC 7800 or for procedure 7300B (FIG. 7C) for aerodynamic diameter-ready OPC 7900.

Referring again to FIG. 7A, at step 7400 the user determines if there is enough calibration data, depending on the desired accuracy of results and the time available (the higher the accuracy desired, the longer it takes due to need for more calibration data). Once calibration for either one (7300A or 7300B) is complete at step 7400, the next step 7500 is to find the optimal refractive index and shape factor using the calibration data set. Step 7500 can then be subdivided into 3 subflows: Flow 7500A (FIG. 7D) for determining optimal refractive index and shape factor for mobility diameter using one calibration data; Flow 7500B (FIG. 7E) for determining optimal refractive Index and shape factor for mobility using multiple calibration data; and Flow 7500C (FIG. 7F) for determining optimal refractive index and shape factor for aerodynamic diameter using multiple calibration data.

Referring back to FIG. 7A, once the optimal refractive index and shape factors are found, the next step 7600 is to generate a new calibration curve using the acquired optimal refractive index and shape factor. At step 7700, a resizing operation of the polydisperse aerosols measured in the first step with the new calibration curve is then performed. At this point, depending on the original calibration, the process bifurcates to step 7800 to be a mobility diameter-ready OPC or to step 7900 to be an aerodynamic diameter-ready OPC.

Figure 7B:
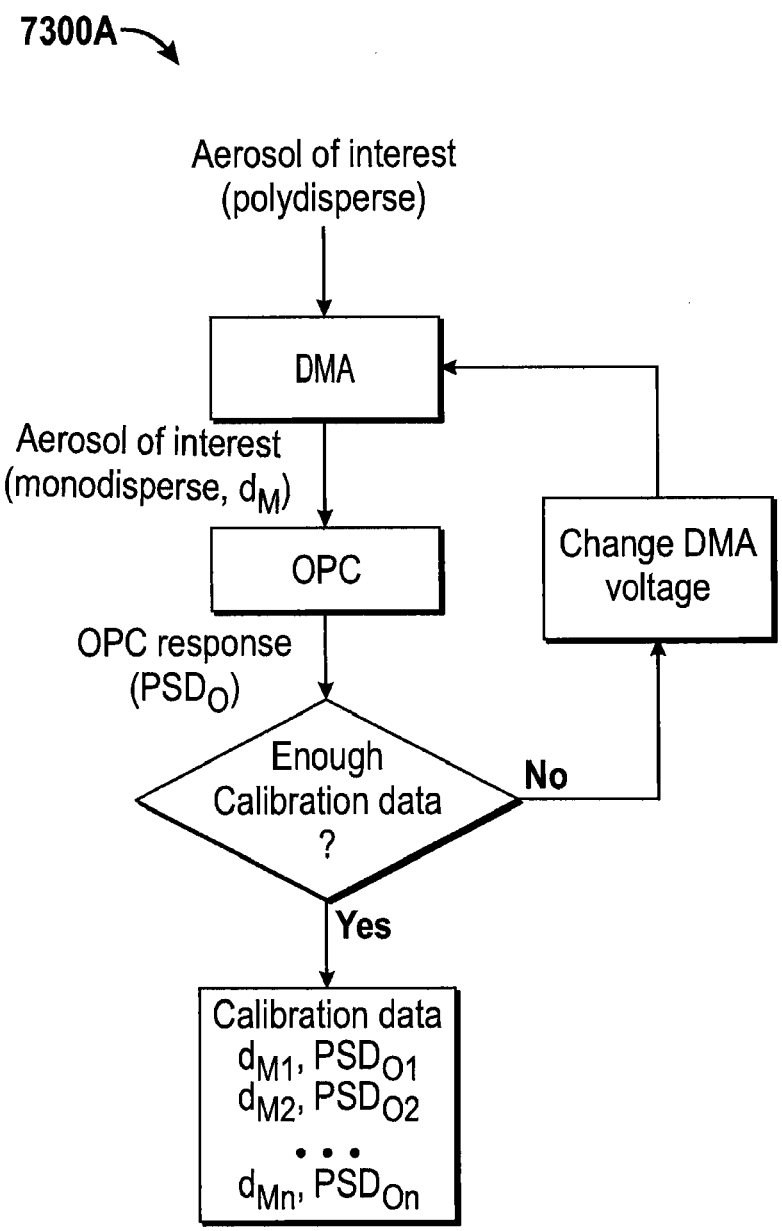

Referring now more specifically to FIG. 7B and mobility calibration process 7300A for the mobility-ready OPC 7800, a particle and an aerosol of interest (polydisperse) is introduced to the DMA thereby generating particle mobility data for one particular size particle which is then input into the OPC to generate a response. If there is enough calibration data, then the calibration data for each particle along with its optical diameter is generated. If more calibration data is needed, the DMA voltage is changed to generate another single size particle which is then input into the OPC to generate another optical response.

Figure 7C:
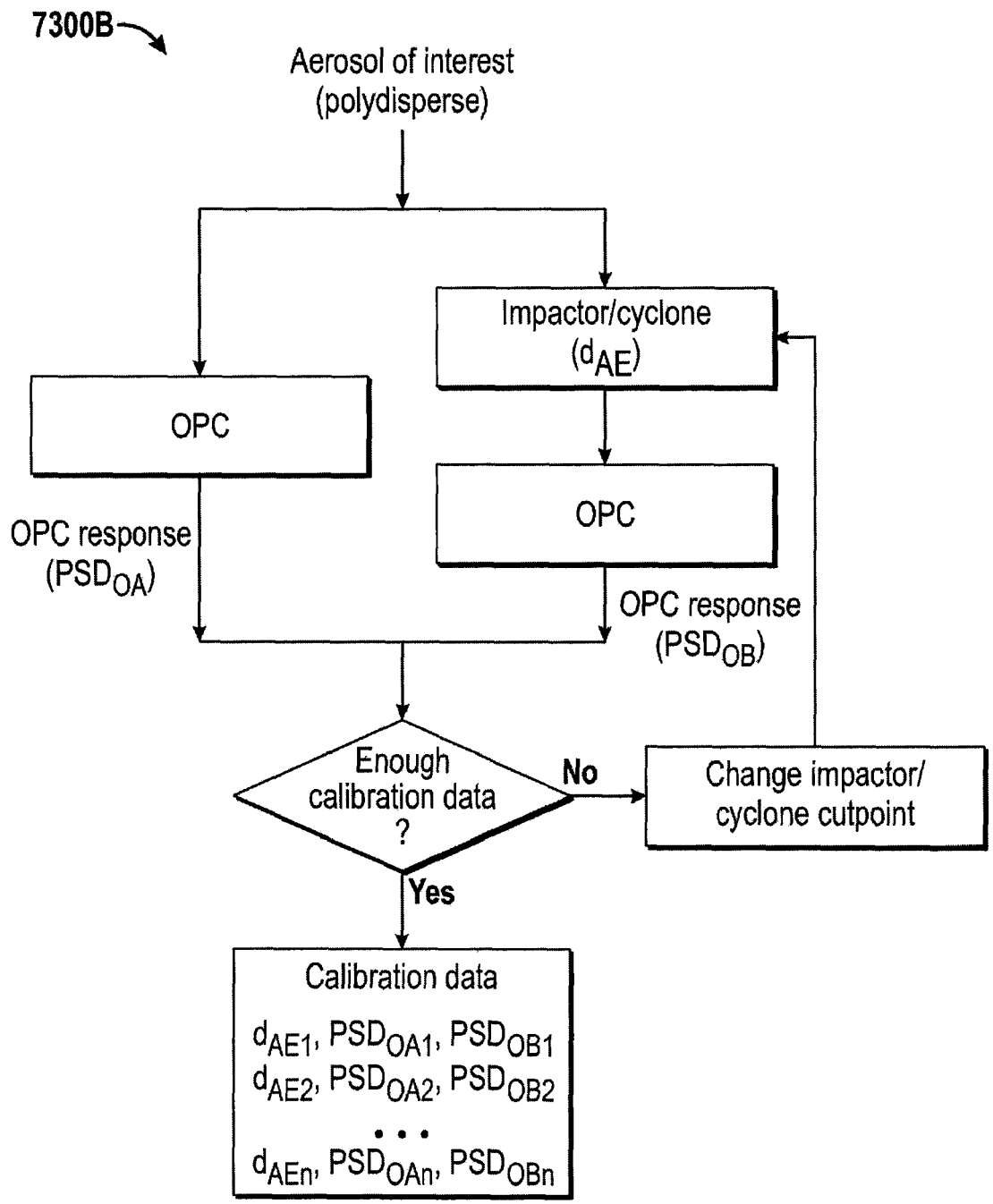

Referring now more specifically to FIG. 7C for procedure 7300B for aerodynamic diameter-ready OPC 7900, an aerosol of interest (polydisperse) is introduced first to the OPC to generate optical diameters of the particles of interest. The particle flow is also introduced to the impactor/cyclone to generate aerodynamic diameters with its flow than being introduced to the OPC to then generate optical diameters of the particles of interest. If there is enough calibration data, then the calibration data for each particle along with its optical diameter is generated for each of its aerodynamic diameter (with and without the impactor/cyclone data). If more calibration data is needed, the cut point for the impactor/cyclone is changed and then the particle is measured again in the impactor/cyclone path and moves back through to the OPC to then determine if there is enough calibration data.

Figure 7D:
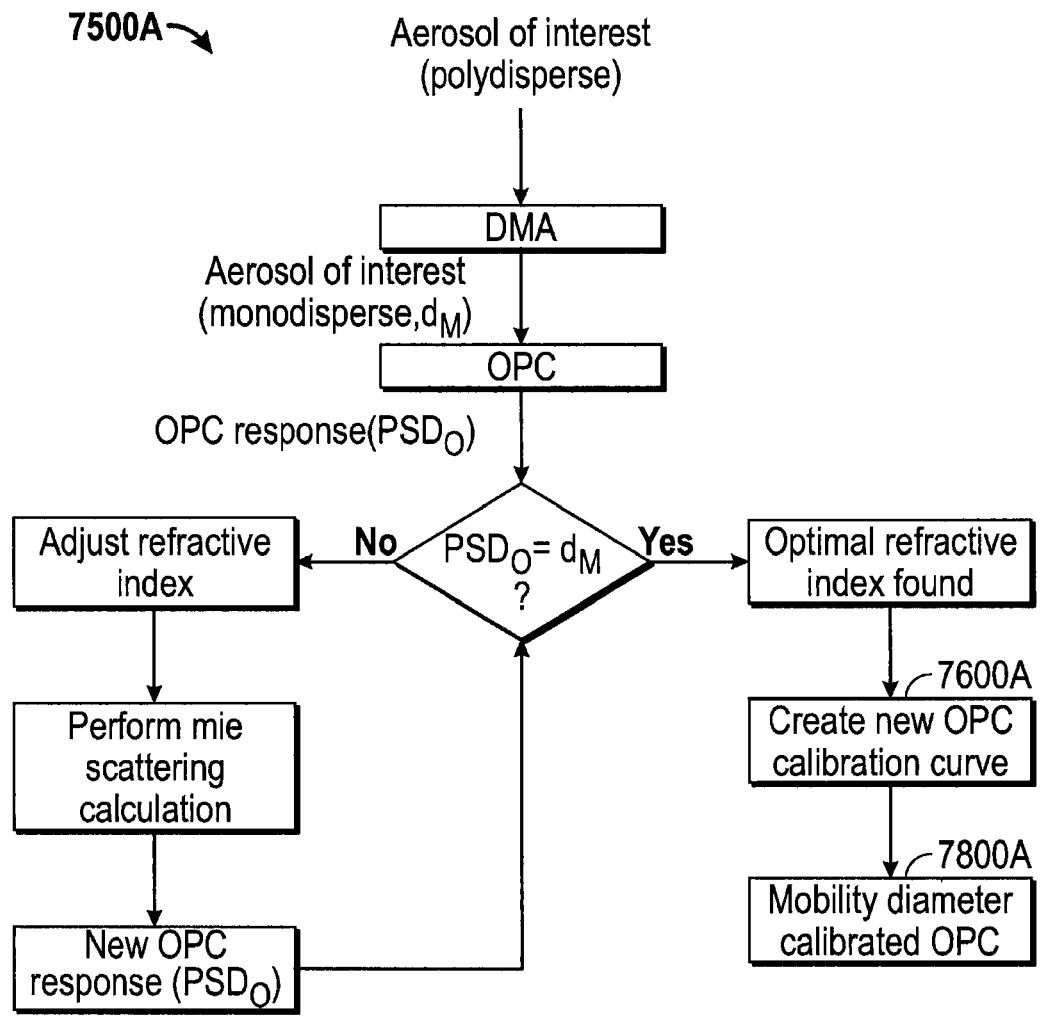

Referring now more specifically to FIG. 7D (and step 7500 of FIG. 7A), subflow 7500A illustrates how to determine the optimal refractive index and shape factor for mobility diameter using one calibration data by first introducing the aerosol of interest (polydisperse) to the DMA thereby generating particle mobility data for one particular size particle which is then input into the OPC to generate a response. If the particle optical diameter is equal to the mobility diameter then the optimal refractive index has been found which leads to generating a new OPC calibration curve 7600A and then a mobility diameter calibrated OPC 7800A. On the other hand, if the particle optical diameter is not equal to the mobility diameter then the refractive index is adjusted, thereafter performing a Mie scattering calculation which then generates a new OPC response or optical diameter. This keeps cycling until the particle optical diameter is equal to the mobility diameter then the optimal refractive index has been found and then it moves to the righthand of flow 7500A leading to creating a new OPC calibration curve 7600A as discussed above.

Figure 7E:
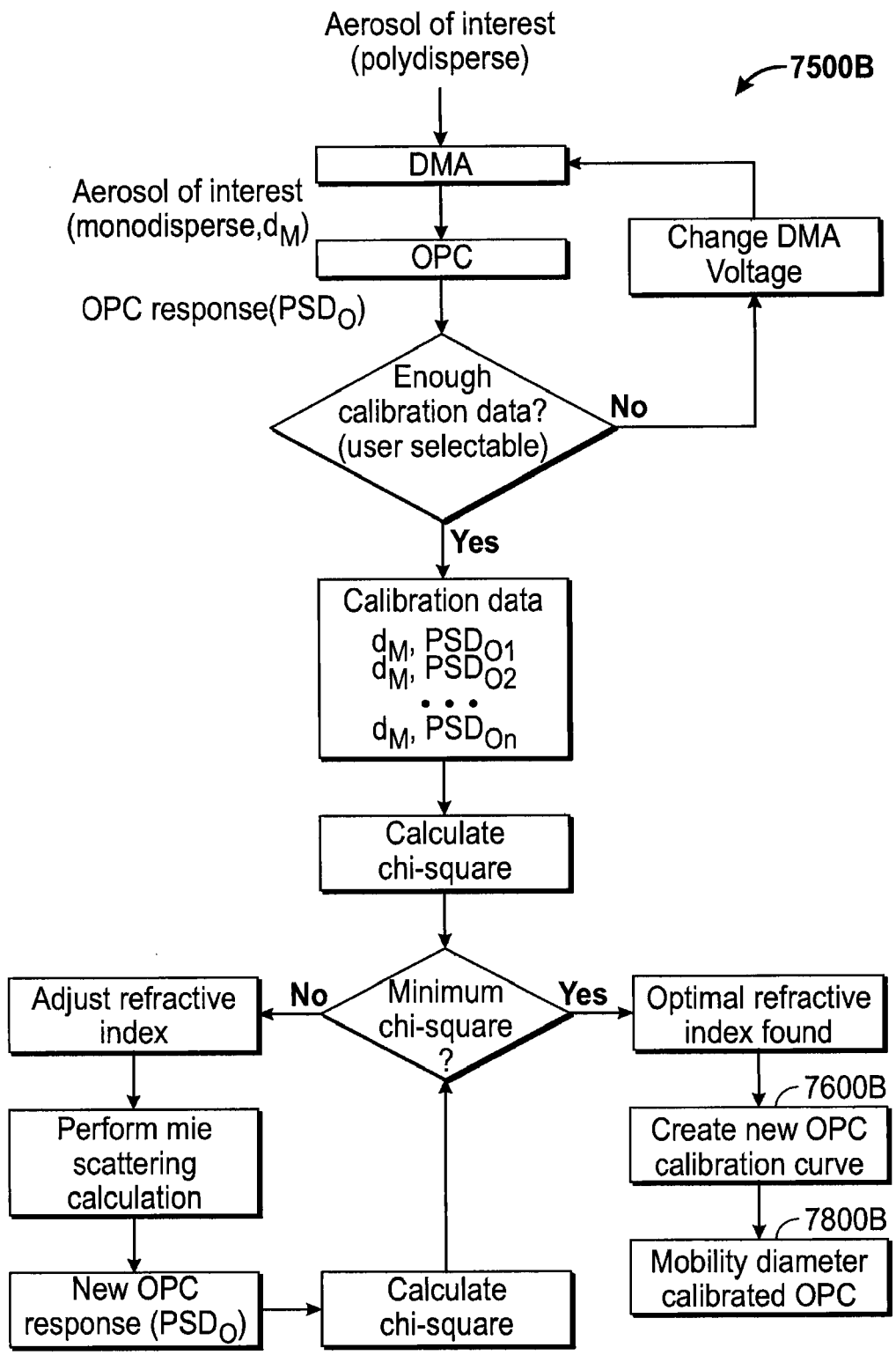

Referring now more specifically to FIG. 7E (and step 7500 of FIG. 7A), subflow 7500B illustrates how to determine the optimal refractive index and shape factor for mobility using multiple calibration data. The aerosol of interest (polydisperse) is introduced to the DMA thereby generating particle mobility data for one particular size particle which is then input into the OPC to generate a response. If there is enough calibration data, then the calibration data for each particle along with its optical diameter is generated. If more calibration data is needed, the DMA voltage is change and then the particle is measured again in the DMA and back through to the OPC. Once the calibration data generated then the chi-square is calculated and its determined if we have reached the minimum chi-square, if so then the optimal refractive index has been found which leads to generating a new OPC calibration curve 7600B and then a mobility diameter calibrated OPC 7800B. On the other hand, if the minimum chi-square is not found then the refractive index is adjusted, thereafter performing a Mie scattering calculation. This in turn generates a new OPC response or optical diameter and thereafter another chi-square is calculated and compared with a minimum chi-square. This keeps cycling until the minimum chi-square is reached then the optimal refractive index has been found and then it moves to the righthand of flow 7500B leading to creating a new OPC calibration curve 7600B as discussed above.

Figure 7F:
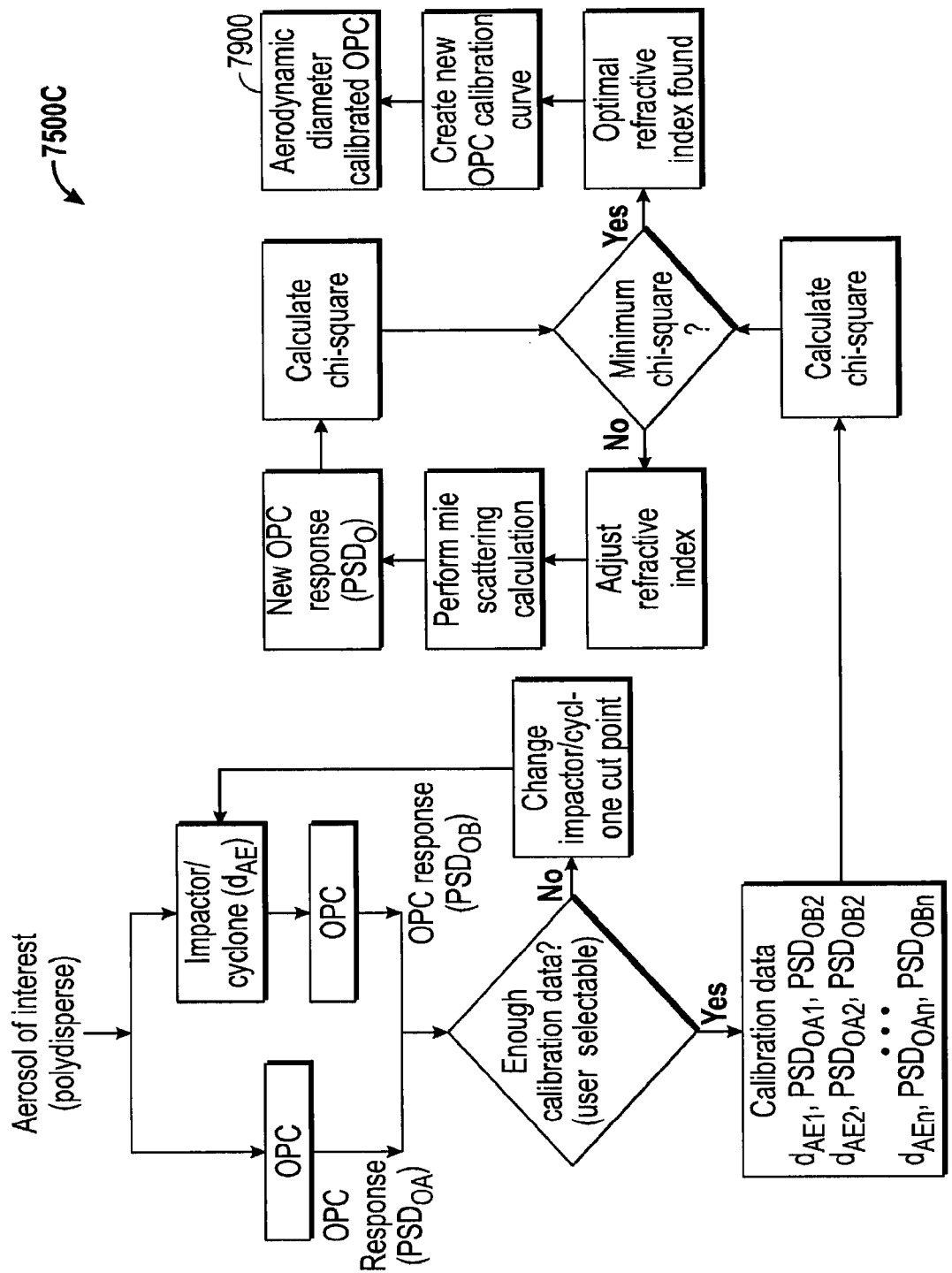

Referring now more specifically to FIG. 7F (and step 7500 of FIG. 7A), subflow 7500C illustrates how to determine the optimal refractive index and shape factor for aerodynamic diameter using multiple calibration data. The aerosol of interest (polydisperse) is introduced first to the OPC to generate optical diameters of the aerosol particles of interest. The particle flow is also introduced to the impactor/cyclone to generate aerodynamic diameters with its flow than being introduced to the OPC to then generate optical diameters of the particles of interest. If there is enough calibration data, then the calibration data for each particle along with its optical diameter is generated for each of its aerodynamic diameter (with and without the impactor/cyclone data). If more calibration data is needed, the cut point for the impactor/cyclone is changed and then the particle is measured again in the impactor/cyclone path and moves back through to the OPC to then determine if there is enough calibration data. Once the calibration data is generated then the chi-square is calculated and its determined if we have reached the minimum chi-square, if so then the optimal refractive index has been found which leads to generating a new OPC calibration curve and then an aerodynamic diameter calibrated OPC 7900C. On the other hand, if the minimum chi-square is not found then the refractive index is adjusted, thereafter performing a Mie scattering calculation. This in turn generates a new OPC response or optical diameter and thereafter another chi-square is calculated and compared with a minimum chi-square. This keeps cycling until the minimum chi-square is reached then the optimal refractive index has been found and then it moves to the righthand of flow 7500C leading to creating a new OPC calibration curve as discussed above.

In a related embodiment, a DMA and OPS particle sizing system includes a switch to allow for re-calibration by having the particle flow only to the DMA and then once its re-calibrated then the system switches back over to having the particle flow through both the DMA and the OPS.

Referring now to FIG. 8, in this example embodiment of the measurement system, 8000, an SMPS system used in this work was a TSI Model 3936 with a differential mobility analyzer (DMA) and condensation particle counter (CPC) being an LDMA Model 3081 and CPC Model 3010, respectively. The size range was 10 nm to about 500 nm. The OPC used in this work was a high resolution optical particle spectrometer TSI 3330 Optical Particle Sizer (OPS). The OPS is a light portable, battery-powered unit that is capable of detecting particles from 0.3 to 10 µm in diameter in up to 16 channels. The channel boundaries are user adjustable. The OPS also features real-time Mie scattering calculation capability.

In this example embodiment of the measurement method, a polydisperse aerosol was first measured by the SMPS and OPS simultaneously. To calibrate the OPS for mobility diameter, several DMA classified monodisperse aerosols were measured by the OPS. To improve data quality, the size channel boundaries of the OPS were adjusted so that all 16 channels were allocated over the narrow range from 0.3 to 1.0 µm for high resolution measurement. Mie scattering calculations were then performed to find the optimal refractive index that minimized the difference between the mobility diameters of these monodisperse aerosols from the DMA and optical diameters from the OPS. The shape factor was also used to further improve the results. This calibration step is illustrated in FIG. 2. Once the optimal refractive index and shape factor were determined, a new calibration curve was generated, and OPS polydisperse aerosol distributions measured in the first step were then resized with this new calibration curve. The resized OPS polydisperse distributions were subsequently merged with the SMPS distributions to obtain wide range aerosol size distributions. Challenge aerosols: Methylene blue, Dioctyl sebacate (DOS or DEHS), and ambient aerosols measured at various locations.

Distributions of a laboratory generated methylene blue aerosol measured with SMPS and OPS were previously shown in FIGS. 5 and 6. Agreement between the SMPS distribution and OPS distribution with the refractive index correction in the overlapping region is clearly better than the OPS distribution without the correction. Ambient aerosol size distributions measured with the SMPS and OPS at one location are illustrated in FIG. 5, while another location, designated as a smoking area, appears as the second peak in FIG. 6 and is believed to be particles generated from cigarettes.

A method was successfully developed to convert optical diameters to mobility diameters without the knowledge of aerosol shape and optical properties. Without the refractive index adjustment and shape factor correction, it was found that optical diameters could be quite different from the mobility diameters if the refractive indices of the aerosols were very different from the PSL aerosols (such as methlyne blue aerosol) and/or aerosols were nonspherical. The disclosed method is more robust than merging SMPS and OPS distributions by minimizing the count differences between the two measurement techniques, since the merged distributions by the latter method could be significantly biased by instrument counting efficiencies in the overlapping region.

In one example embodiment, a measurement system for measuring aerosol size distribution includes an electromagnetic radiation source operatively coupled with beam shaping optics for generation of a beam of electromagnetic radiation; an inlet nozzle for passage of an aerosol flow stream therethrough, said aerosol flow stream containing particles and intersecting said beam of electromagnetic radiation to define an interrogation volume, said particles scattering said electromagnetic radiation from said interrogation volume; and a radiation collector for collection of a portion of said electromagnetic radiation scattered from the particles in said interrogation volume. A detector is also included for detection of said portion of said electromagnetic radiation collected by said radiation collector, along with a calibration system for generating one or more sets of calibration data from a particle of an aerosol of interest, said calibration system operatively coupled to said detector. The system also includes digital processing means for computing an aerodynamic diameter and/or mobility diameter from an optical diameter operatively coupled to said calibration system, said digital processing means configured to generate a Mie light scattering model to determine a refractive index of the particles of an aerosol of interest using the calibration data and then convert the optical diameters to aerodynamic diameters and/or mobility diameters using the resulting refractive index.

In a related embodiment, the measurement system has a calibration system that is an electrical mobility device adapted to generate predefined electrical mobility size distributions or electrical mobility cut points. The electrical mobility device is selected from the group consisting of a differential mobility analyzer and electrostatic precipitator.

In another related embodiment, the measurement system further includes a scanning mobility particle sizing device operatively coupled to the detector thereby providing a wide particle range sizing system adapted to measure a mass of particles having a lower limit defined as being between about 10 nm and about 500 nm and an upper limit defined as being between about 300 nm and about 10 µm.

In yet another related embodiment, the measurement system has a calibration system that is an aerodynamic diameter device adapted to generate aerodynamic diameter cut points. The aerodynamic diameter device is an impactor or a set of impactors with different aerodynamic cut points. In a related embodiment, the aerodynamic diameter device is a cyclone or a set of cyclones with different aerodynamic cut points.

In another example embodiment, an instrument for measuring aerosol size distribution includes an electromagnetic radiation source operatively coupled with beam shaping optics for generation of a beam of electromagnetic radiation; an inlet nozzle for passage of an aerosol flow stream there through, said aerosol flow stream containing particles and intersecting said beam of electromagnetic radiation to define an interrogation volume, said particles scattering said electromagnetic radiation from said interrogation volume; and a radiation collector for collection of a portion of said electromagnetic radiation scattered from said interrogation volume. The instrument also includes a detector for detection of said portion of said electromagnetic radiation collected by said radiation collector; and digital processing means for computing a Mie light scattering model and adapted to incorporate optical properties of the particles in an aerosol of interest as part of the particle measurement, said digital processing means operatively coupled to said detector. In a related embodiment, digital processing means is also configured to convert optical diameters of the particles to aerodynamic diameters and/or electrical mobility diameters, said digital processing means operatively coupled to said detector.

In another example embodiment, a method for determining electrical mobility aerosol size distribution includes providing a detector to receive electromagnetic radiation scattered from an interrogation volume and causing particles to flow through said interrogation volume and scatter electromagnetic radiation onto said detector to generate an electrical signal from said detector. The method also includes generating a plurality of pulse height outputs from said electrical signal with said pulse height signal conditioner, each of said pulse height outputs corresponding to a particle passing through said interrogation volume and corresponding to an optical particle size, and includes generating one or more sets of calibration data with a calibration system from the passing particles. The method further includes the step of determining a refractive index of the particle of an aerosol of interest using the calibration data and a Mie light scattering model, and converting optical diameters of said passing particles to electrical mobility diameters.

In one related embodiment, the method includes providing as the calibration system an electrical mobility device which is capable of generating narrow electrical mobility size distributions or providing known electrical mobility cut points, wherein the electrical mobility device is selected from the group consisting a differential mobility analyzer and an electrostatic precipitator.

In yet another example embodiment, a method for determining aerodynamic aerosol size distribution includes providing a detector to receive electromagnetic radiation scattered from an interrogation volume, and causing particles to flow through said interrogation volume and scatter electromagnetic radiation onto said detector to generate an electrical signal from said detector. The method also includes generating a plurality of pulse height outputs from said electrical signal with said pulse height signal conditioner, each of said pulse height outputs corresponding to a particle passing through said interrogation volume and corresponding to an optical particle size, and generating one or more sets of calibration data with a calibration system from the passing particles. The method further includes determining a refractive index of the particles of an aerosol of interest using the calibration data and a Mie light scattering model, and converting optical diameters of said passing particles to aerodynamic diameters. In a related embodiment, the calibration system is an aerodynamic diameter device adapted to generate at least one predefined aerodynamic diameter cut point, wherein the aerodynamic diameter device is an impactor or a set of impactors with different cut points. In another embodiment, the aerodynamic diameter device is a cyclone or a set of cyclones with different cut points.

In yet another example embodiment, a method for determining size segregated aerosol mass concentration includes providing a detector to receive electromagnetic radiation scattered from an interrogation volume, and causing particles to flow through said interrogation volume and scatter electromagnetic radiation onto said detector to generate an electrical signal from said detector. The method also includes generating a plurality of pulse height outputs from said electrical signal with said pulse height signal conditioner, each of said pulse height outputs corresponding to a particle passing through said interrogation volume and corresponding to an optical particle size and generating one or more sets of calibration data with a calibration system. The method further includes determining the optimal/effective refractive index of the aerosol of interest using the calibration data and the Mie light scattering model, converting optical diameters to aerodynamic diameters, and calculating a size segregated mass concentration from said aerodynamic diameters.

In a related embodiment, the calibration system of the method is an aerodynamic device which generates one or more known aerodynamic diameter cut points, wherein the aerodynamic device is an impactor or a set of impactors with different aerodynamic cut points. In another embodiment, the aerodynamic device is a cyclone or a set of cyclones with different aerodynamic cut points.

The following patents that relate to OPC devices are herein incorporated by reference in their entirety and constitute part of the disclosure herein: U.S. Pat. Nos. 6,831,279; 5,561,515; 5,895,922; 6,639,671; 7,066,037; and 7,167,099 and 7,932,490. Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

I claim:

1. A measurement system for measuring aerosol size distribution, comprising:
   an electromagnetic radiation source operatively coupled with beam shaping optics for generation of a beam of electromagnetic radiation;
   an inlet nozzle for passage of an aerosol flow stream therethrough, said aerosol flow stream containing particles and intersecting said beam of electromagnetic radiation to define an interrogation volume, said particles scattering said electromagnetic radiation from said interrogation volume;
   a radiation collector for collection of a portion of said electromagnetic radiation scattered from said interrogation volume;
   a detector for detection of said portion of said electromagnetic radiation collected by said radiation collector; and
   a digital processor configured to generate one or more sets of calibration data from polydisperse particles in the aerosol, the calibration data including at least one of electrical mobility diameter and optical diameter data pairs and aerodynamic diameter and optical diameter data pairs, and perform a Mie scattering calculation on at least one of the mobility diameter and optical diameter data pairs and the aerodynamic diameter and optical diameter data pairs so as to determine a refractive index for the polydisperse aerosol for each data pair, the digital processor further configured to generate calibration curves using the refractive index of the mobility diameter and optical diameter pairs to enable the aerosol measurement system to perform an electrical mobility diameter measurement for the particles in the aerosol, the digital processor further configured to generate calibration curves using the refractive index of the aerodynamic diameter and optical diameter pairs to enable the aerosol measurement system to perform an aerodynamic diameter measurement for particles in the aerosol, said digital processor operatively coupled to said detector.

2. A measurement system for measuring aerosol size distribution, comprising:
- an electromagnetic radiation source operatively coupled with beam shaping optics for generation of a beam of electromagnetic radiation;
- an inlet nozzle for passage of an aerosol flow stream therethrough, said aerosol flow stream containing particles and intersecting said beam of electromagnetic radiation to define an interrogation volume, said particles scattering said electromagnetic radiation from said interrogation volume;
- a radiation collector for collection of a portion of said electromagnetic radiation scattered from the particles in said interrogation volume;
- a detector for detection of said portion of said electromagnetic radiation collected by said radiation collector;
- a calibration system for generating one or more sets of calibration data from particles in the aerosol, the calibration data including at least one of electrical mobility diameter and optical diameter data pairs and aerodynamic diameter and optical diameter data pairs, said calibration system operatively coupled to said detector; and
- a digital processor operatively coupled to said calibration system and configured to generate a Mie light scattering model to determine a refractive index and a shape factor using the calibration data, the digital processor further configured to generate calibration curves using the refractive index and shape factor and use the calibration curves to re-size the particles in the aerosol, thereby enabling the aerosol measurement system to perform either an electrical mobility diameter measurement or an aerodynamic diameter measurement for the particles in the aerosol.

3. The measurement system of claim 2 wherein the calibration system includes an electrical mobility device adapted to generate predefined electrical mobility size distributions or electrical mobility cut points.

4. The measurement system of claim 3 wherein the electrical mobility device is selected from the group consisting of a differential mobility analyzer and electrostatic precipitator.

5. The measurement system of claim 3 further including a scanning mobility particle sizing device operatively coupled to the detector thereby providing a wide particle range sizing system adapted to measure a mass of particles having a lower limit defined as being between about 10 nm and about 500 nm and an upper limit defined as being between about 300 nm and about 10 μm.

6. The measurement system of claim 2 wherein the calibration system includes an aerodynamic diameter device adapted to generate aerodynamic diameter cut points.

7. The calibration system of claim 6 wherein the aerodynamic diameter device includes an impactor or a set of impactors with different aerodynamic cut points.

8. The calibration system of claim 6 wherein the aerodynamic diameter device includes a cyclone or a set of cyclones with different aerodynamic cut points.

* * * * *